(12) United States Patent
Nathanson

(10) Patent No.: US 7,285,103 B2
(45) Date of Patent: Oct. 23, 2007

(54) STRAP TENSION INDICATOR FOR ORTHOPEDIC BRACE

(75) Inventor: Jeremy J. Nathanson, Vista, CA (US)

(73) Assignee: DJO, LLC, Vista, CA (US)

( * ) Notice: Subject to any disclaimer, the term of this patent is extended or adjusted under 35 U.S.C. 154(b) by 760 days.

(21) Appl. No.: 10/753,088

(22) Filed: Jan. 7, 2004

(65) Prior Publication Data

US 2005/0148917 A1    Jul. 7, 2005

(51) Int. Cl.
*A61F 5/00* (2006.01)
*A44B 19/00* (2006.01)

(52) U.S. Cl. .................. 602/16; 24/593.11; 602/5; 602/20; 602/23

(58) Field of Classification Search ........... 24/593.1, 24/633, DIG. 48, DIG. 51, DIG. 60, 596.1, 24/591.1, 648; 602/5, 23, 16, 26
See application file for complete search history.

(56) References Cited

U.S. PATENT DOCUMENTS

| 3,613,679 | A | 10/1971 | Bijou |
| 4,457,251 | A | 7/1984 | Weman et al. |
| 4,991,571 | A | 2/1991 | Kausek |
| 5,111,806 | A | 5/1992 | Travis |
| 5,503,620 | A | 4/1996 | Danzger |
| 5,779,659 | A | 7/1998 | Allen |
| 6,050,967 | A | 4/2000 | Walker et al. |
| 6,152,893 | A | 11/2000 | Pigg et al. |
| 6,325,773 | B1 | 12/2001 | Opel |
| 6,338,723 | B1 | 1/2002 | Carpenter et al. |
| 7,117,569 | B2 * | 10/2006 | Bledsoe .............. 24/593.11 |
| 2003/0045826 | A1 | 3/2003 | Meyer |
| 2003/0078528 | A1 | 4/2003 | Rahman et al. |

* cited by examiner

*Primary Examiner*—Kim M. Lewis
(74) *Attorney, Agent, or Firm*—Knobbe, Martens, Olson and Bear LLP

(57) ABSTRACT

A strap tension indicator for orthopedic brace is provided. Certain embodiments include a strap tab cap that is slidable relative to a rigid brace frame member. As tension in the strap increases or decreases, the strap tab cap slides with respect to the frame member, covering and uncovering various indicator portions on the frame member. Certain other embodiments include a strap tab that is slidable relative to a strap tab cap. As tension in the strap increases or decreases, the strap tab slides relative to the strap tab cap, covering and uncovering various indicator portions on the strap tab and/or the frame member. The strap tension indicator provides positive indication of optimal strap tension. Certain embodiments also provide positive indication of inadequate or excessive strap tension.

47 Claims, 8 Drawing Sheets

STRAP TENSION INDICATOR FOR ORTHOPEDIC BRACE

BACKGROUND OF THE INVENTION

1. Field of the Invention

The present invention relates to orthopedic braces. More particularly, the present strap tension indicator for orthopedic brace provides a positive indication of optimal strap tension.

2. Description of the Related Art

Orthotic braces stabilize and protect joints, such as the knee. In many of these braces, straps fasten the brace to the limb and enable the brace to apply forces to the limb. The amount of tension in a strap affects the function, fit, and comfort of a brace. Inadequate tension can diminish the ability of the brace to stabilize or protect the limb, and can prevent the brace from staying in place on the limb. On the other hand, too much tension can cause discomfort for the wearer and restrict the wearer's blood flow. Therefore, orthotic brace wearers would benefit from a device that indicates whether the brace straps are properly tensioned for optimal function, fit, and comfort of the brace.

U.S. Pat. No. 6,050,967 to Walker et al. discloses a bandage compression indicator. Yarn in the bandage provides a continuous pattern of repeating geometric shapes. Each shape deforms as tension in the bandage increases. Thus, the appearance of the shapes indicates the tension in the bandage, and hence the compression force applied to the wearer by the bandage.

U.S. Pat. No. 5,503,620 to Danzger discloses a back support belt. The back support belt comprises a primary support belt and a secondary tensioning belt that fits around the primary support belt. Both belts include fasteners at the front area of the wearer's waist. The secondary tensioning belt includes colored tension indicators that are visible only from the rear and side areas of the wearer. The colored tension indicators on the secondary tensioning belt comprise a white band and red bands at either end of the white band. When the secondary tensioning belt is at zero tension, central tunnel members cover the white band and leave the red bands visible. When a wearer applies the back support belt, he or she first fastens the primary support belt around his or her waist. He or she then fastens the secondary tensioning belt around the primary support belt. While fastening the secondary tensioning belt, the wearer pulls the ends of the belt until the tension draws the white band out from under the central tunnel members, and pulls the red bands under a pair of outer tunnel members. When only the white bands are visible, the belt is properly tensioned. If the belt tension decreases, the red bands creep out from under the outer tunnel members and become visible again, indicating that the belt must be re-tensioned.

Unfortunately, the prior art embodies several disadvantages. For example, the prior art does not provide a strap tension indicator within a rigid orthopedic brace, such as a knee brace. Therefore, a strap tension indicator that indicates strap tension in a rigid orthopedic brace would be of great benefit to people who wear rigid orthopedic braces.

SUMMARY OF THE INVENTION

The preferred embodiments of the present strap tension indicator for orthopedic brace have several features, no single one of which is solely responsible for their desirable attributes. Without limiting the scope of this strap tension indicator as expressed by the claims that follow, its more prominent features will now be discussed briefly. After considering this discussion, and particularly after reading the section entitled "Detailed Description of the Preferred Embodiments," one will understand how the features of the preferred embodiments provide advantages, which include positive indication of strap tension, an unobtrusive, low-profile design that does not significantly alter the cosmetic appearance of the brace, the capability to be adjusted to provide tension indication for any brace strap regardless of the magnitude of the ideal tension for that particular strap, and very few moving parts, thus providing the indicator with a long life span.

A preferred embodiment of the present strap tension indicator for orthopedic brace comprises a rigid brace frame member including an aperture, a resilient member located within the aperture, a strap tab and a fastening member cooperating with the aperture to secure the strap tab to the rigid brace member. In a first position, the fastening member abuts the resilient member. The strap tab and the fastening member are movable together toward a second position in which the resilient member tends to push the strap tab and the fastening member back toward the first position.

Another preferred embodiment of the present strap tension indicator for orthopedic brace comprises a method of indicating the tension in a strap for an orthopedic brace. The method comprises the steps of providing an orthopedic brace having at least a first strap and a rigid brace member, providing on the rigid brace member an indicator, and applying tension to the strap. The first strap includes a strap tab that is secured to the rigid brace member and capable of moving with respect to the rigid brace member between a first position and a second position. The tension causes the strap tab to move from the first position to the second position, thereby altering an appearance of the indicator.

Another preferred embodiment of the present strap tension indicator for orthopedic brace comprises a rigid brace frame member, a strap tab slidably secured to the frame member, and a resilient member. The strap tab is movable relative to the frame member between a first position and a second position. The resilient member biases the strap tab towards the first position.

Another preferred embodiment of the present strap tension indicator for orthopedic brace comprises a rigid brace frame member, a strap tab slidably secured to the frame member and a resilient member. The strap tab is movable relative to the frame member between a first position and a second position. The resilient member biases the strap tab towards the first position. The indicator further comprises means for indicating when the strap tab occupies the first position and when the strap tab occupies the second position.

Another preferred embodiment of the present strap tension indicator for orthopedic brace comprises a rigid brace frame member including an aperture, and a resilient member located within the aperture. The indicator further comprises a strap and a fastening member partially within the aperture to secure the strap to the rigid brace member. In a first position, the fastening member abuts the resilient member. The strap and the fastening member are movable together toward a second position in which the resilient member tends to push the strap and the fastening member back toward the first position.

Another preferred embodiment of the present strap tension indicator for orthopedic brace comprises a rigid brace frame member and a strap secured to the frame member. The strap is movable relative to the frame member between a first position and a second position. The indicator further comprises a resilient member. The resilient member biases the strap towards the first position.

BRIEF DESCRIPTION OF THE DRAWINGS

The preferred embodiments of the present strap tension indicator for orthopedic brace, illustrating its features, will now be discussed in detail. These embodiments depict the novel and non-obvious strap tension indicator shown in the accompanying drawings, which are for illustrative purposes only. These drawings include the following figures, in which like numerals indicate like parts.

DETAILED DESCRIPTION OF THE PREFERRED EMBODIMENTS

Figure 1:
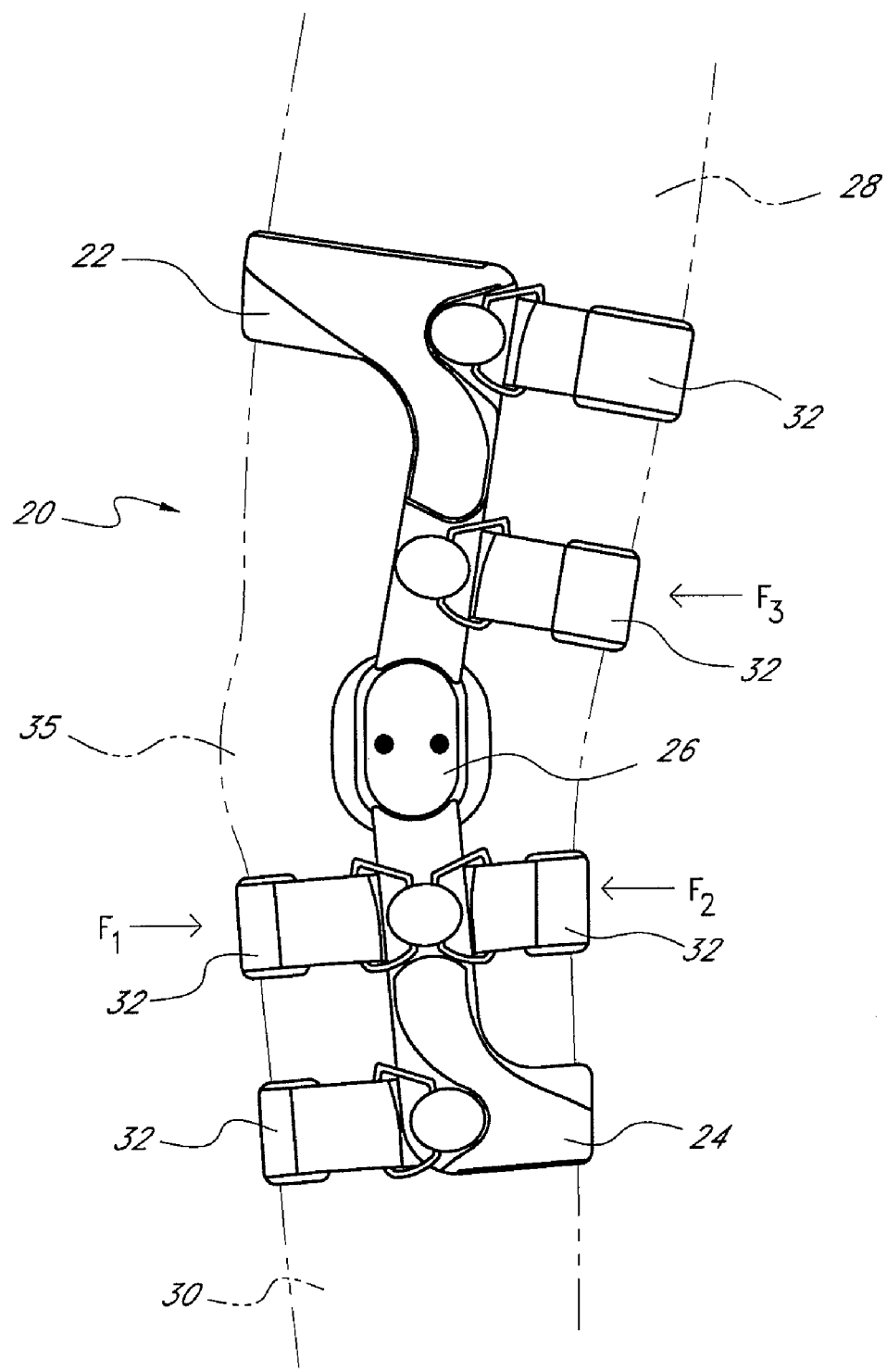
FIG. 1 is a right-side elevational view of a typical knee brace.

FIG. 1 illustrates a typical knee brace 20. The brace 20 is readily modified to include the present strap tension indicator. Those of skill in the art will appreciate that the particular configuration of cuffs and straps shown merely illustrates one example of a use for the present strap tension indicator. The present strap tension indicator is useful in knee braces having alternate configurations. Furthermore, although the strap tension indicator is illustrated herein within the context of a knee brace, those of skill in the art will appreciate that the strap tension indicator could be used in a variety of other braces. For example, the strap tension indicator could be incorporated into an elbow brace, an ankle brace, a shoulder brace, a back brace, etc.

The brace 20 includes an upper rigid cuff 22 and a lower rigid cuff 24. Hinges 26 located on the medial and lateral sides of the wearer's knee pivotably secure the cuffs 22, 24 to one another. The upper cuff 22 extends around the anterior portion of the wearer's thigh 28, and downward to the hinges 26 along the lateral and medial sides of the wearer's thigh 28. The lower cuff 24 extends around the posterior portion of the wearer's calf 30, and upward to the hinges 26 along the lateral and medial sides of the wearer's calf 30. A plurality of straps 32 extend around the wearer's thigh 28 and lower leg 30.

Tension in each strap 32 applies force to the wearer's leg. A force applied by one strap 32 generates resultant forces in the remaining straps 32 and in the cuffs 22, 24. As described above, the tension in each strap 32 is preferably optimized to provide the brace 20 with the desired function, fit, and comfort. For purposes of illustration, imagine that the brace 20 illustrated in FIG. 1 comprises only the anterior strap 32 just below the wearer's knee 35, and the posterior straps 32 directly adjacent the wearer's knee 35. Tension in the anterior strap 32 creates a force $F_1$ acting in a posterior direction on the wearer's calf 30. The forces acting on the wearer's leg must be in equilibrium, or the brace 20 would not remain on the wearer's leg. Thus, the posterior force $F_1$ generates a resultant anterior force $F_2$ and a resultant anterior force $F_3$. The force $F_2$ acts through the strap 32 on the posterior portion of the wearer's calf, and the force $F_3$ acts through the strap 32 on the posterior portion of the wearer's thigh. The magnitude of the posterior force $F_1$ must be equal to the sum of the magnitudes of the anterior forces $F_2$ and $F_3$.

The present strap tension indicator connects the ends of brace straps to the rigid cuffs of a brace. The indicator provides visual confirmation of optimal strap tension. As described below, in certain embodiments the present strap tension indicator indicates the tension in a single strap, while in certain other embodiments the present strap tension indicator indicates a tension difference between two opposing straps. Those of skill in the art will appreciate that the present strap tension indicator need not be used to connect every strap to a rigid component in a given brace. A brace may employ the present strap tension indicator to connect only some of its straps to its rigid components.

Figure 4:
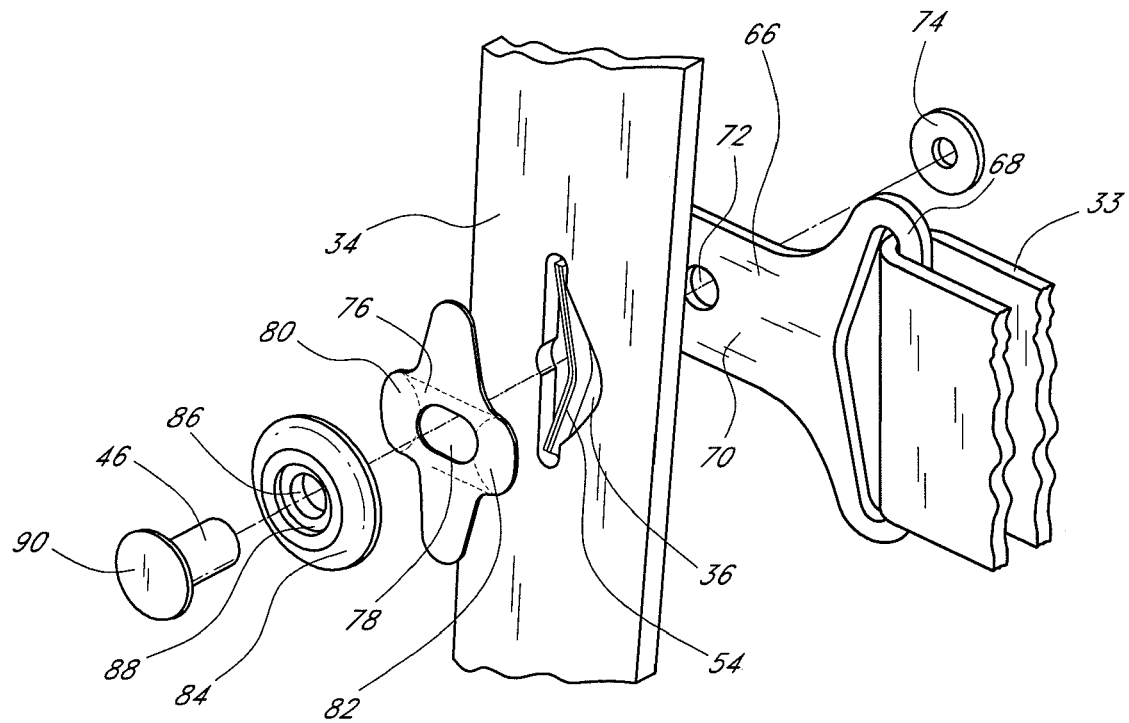
FIG. 4 is an exploded assembly view of the strap tension indicator of FIG. 2, taken from a rear/right-side perspective.
Figure 5:
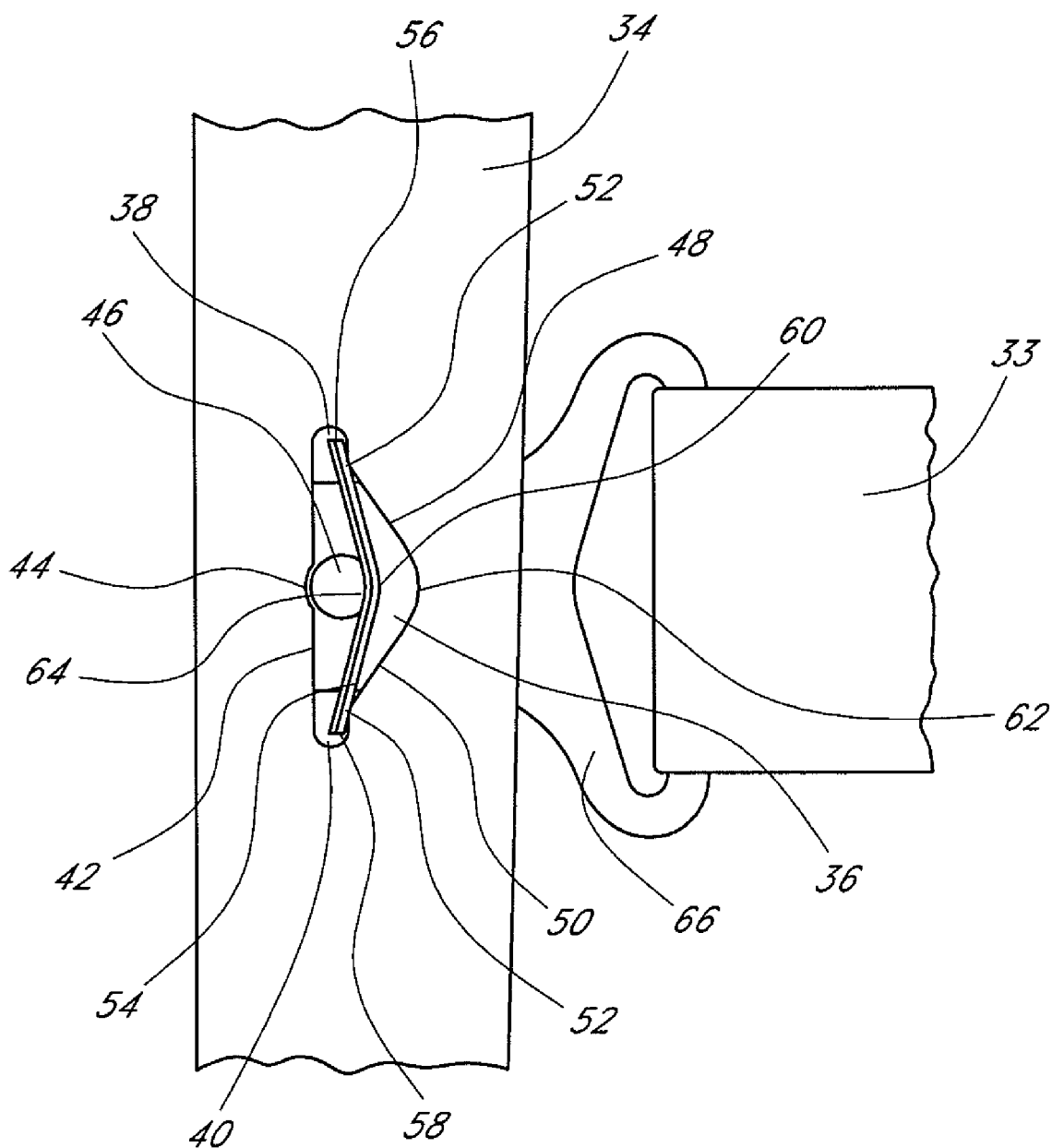
FIG. 5 is a right-side elevational view of the strap tension indicator of FIG. 2, illustrating the rivet, cap and marker label removed to expose the resilient member.

FIG. 4 illustrates in detail a preferred embodiment of the present strap tension indicator. The indicator mounts a strap 33 to a rigid frame member 34 of a brace (not shown). With reference to FIG. 5, the frame member 34 includes an aperture 36. The frame aperture 36 is substantially triangular, with a first corner 38 and a second corner 40 of the triangle being aligned along a longitudinal axis of the frame member 34. A first side 42 of the aperture 36 extending between the first and second corners 38, 40 preferably includes an arcuate indentation 44 that seats a rivet 46, as described below. Second and third sides 48, 50 of the aperture 36 include peaks 52 adjacent the first and second corners 38, 40.

With continued reference to FIG. 5, the aperture 36 houses a resilient member 54. In the illustrated embodiment, the resilient member 54 is a V-shaped leaf spring comprising multiple layers. A preferred material for the resilient member 54 is steel. Those of skill in the art will appreciate that the resilient member 54 could be any other type of resilient device, such as a one-piece leaf spring, a coil spring or a block of resilient material such as polyurethane. The resilient member 54 resists movement of the rivet 46 within the aperture 36, as described below.

In the illustrated embodiment, first and second ends 56, 58 of the resilient member 54 reside in the first and second corners 38, 40, respectively, of the aperture 36. Portions of the resilient member 54 adjacent the first and second ends 56, 58 rest against the peaks 52 in the second and third aperture sides 48, 50. The apex 60 of the V-shaped resilient member 54 resides adjacent and spaced from a third corner 62 of the aperture 36. The crotch 64 of the V-shaped resilient member 54 defines a larger angle than that defined by the aperture third corner 62. Therefore, the resilient member 54 is spaced from the second and third aperture sides 48, 50 over most of its surface area. When the strap 33 is under minimal tension, preferably no portion of the resilient member 54 contacts the aperture second and third sides 48, 50 in the area between the peaks 52.

With reference to FIG. 4, each strap 33 includes a strap tab 66 at either end. A strap tab, as is well known in the art, connects a brace strap to a rigid brace frame member. Those of skill in the art will appreciate that the straps 33 need not be connected to the rigid brace frame members with strap tabs 66. For example, the straps 33 could be connected directly to the rigid brace frame members.

The illustrated strap tab 66 comprises a loop portion 68 that receives the strap 33, and an elongate portion 70 that extends away from the strap end. The elongate portion 70 of the strap tab 66 includes a through hole 72 that is spaced from the strap 33. The rivet 46 passes through the aperture 36 and the strap tab through hole 72, and engages a washer 74 to secure the strap tab 66 to the frame member 34. Those of skill in the art will appreciate that the rivet 46 and washer 74 could be replaced with alternate fastening members, such as a bolt and nut.

When there is minimal tension in the strap 33, as shown in FIG. 5, the rivet 46 seats within the arcuate indentation 44 on the aperture first side 42. The crotch 64 of the V-shaped resilient member 54 abuts the rivet 46 opposite the arcuate indentation 42, thereby retaining the rivet 46 within the arcuate indentation 42.

With reference to FIG. 4, a marker label 76, comprising a flat sheet, abuts the frame member 34 outer surface and overlies the aperture 36. The marker label 76 is preferably a paper or plastic sticker having an adhesive backing that sticks to the frame member 34. The marker label 76 is shaped substantially as a diamond having rounded corners and concave sides. The label 76 thus includes four rounded lobes extending outward from a center of the label 76, with each lobe being oriented ninety-degrees from adjacent lobes. The marker label 76 preferably covers the edges of the aperture 36 to improve the overall appearance of the brace 20 and to prevent dirt and debris from entering the aperture 36. A center portion of the marker label 76 includes an oval-shaped hole 78 through which the rivet 46 passes.

With continued reference to FIG. 4, a first lobe 80 of the marker label 76 resides adjacent the indentation 44 in the aperture first side 42. The first lobe 80 includes a first indicator color, such as green. A second lobe 82 of the marker label 76, opposite the first lobe 80, resides adjacent the aperture third corner 62. The second lobe 82 includes a second indicator color, such as red. Those of skill in the art will appreciate that the colored lobes of the marker label 76 could be replaced by colored portions on the rigid frame member 34 itself, such as painted portions.

A cap 84 overlies the marker label 76. The cap 84 comprises a circular ring having a flat surface (not shown) that abuts the marker label 76. The rivet 46 passes through a central hole 86 in the cap 84. Opposite the flat surface, the cap 84 includes a recess 88 that receives a head 90 of the rivet 46. The rivet 46 thus seats within the cap 84 to provide the brace 20 with a more streamlined appearance. The cap 84 slides freely over the marker label 76 as the rivet 46 moves within the aperture 36 under the influence of tension in the strap 33.

Figure 2:
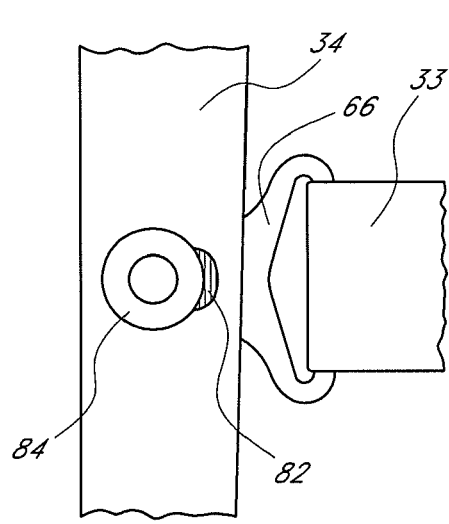
FIG. 2 is a right-side elevational view of a preferred embodiment of the present strap tension indicator, illustrating the indicator in a first position.

When there is minimal tension in the strap 33, the rivet 46 abuts the indentation 44 in the aperture first side 42, as shown in FIG. 5. In this position, the cap 84 covers the first lobe 80 and leaves the second lobe 82 uncovered, as shown in FIG. 2. The visible red color indicates that the tension in the strap 33 is too low.

Figure 3:
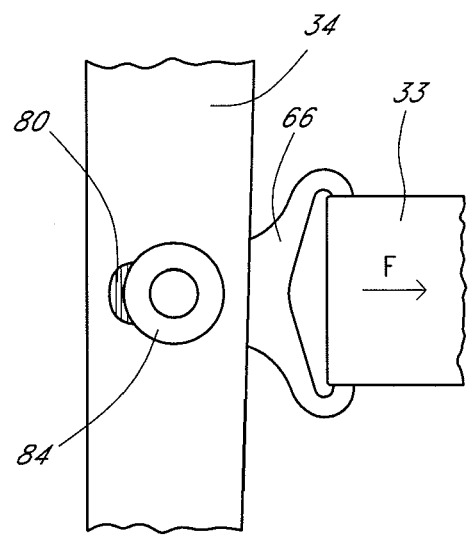
FIG. 3 is a right-side elevational view of the strap tension indicator of FIG. 2, illustrating the indicator in a second position.

With reference to FIG. 5, as tension in the strap 33 increases, the strap tab 66 forces the rivet 46 to bear against the crotch 64 of the resilient member 54. The force of the rivet 46 upon the resilient member 54 flexes the resilient member 54, allowing the rivet 46 to move toward the aperture third corner 62. As the rivet 46 moves, the cap 84 slides across the marker label 76, covering the red colored second lobe 82 and exposing the green colored first lobe 80, as shown in FIG. 3. When the red colored second lobe 82 is completely covered and the green colored first lobe 80 is uncovered, the strap 33 is properly tensioned. If strap tension drops, the resilient member 54 pushes the rivet 46 back toward the indentation 44. As the rivet 46 moves, the cap 84 slides across the marker label 76, covering the green colored first lobe 80 and exposing the red colored second lobe 82, as shown in FIG. 2.

Figure 8:
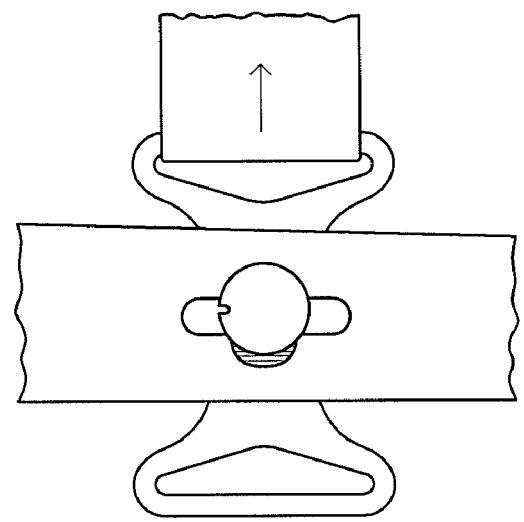
FIG. 8 is a right-side elevational view of the strap tension indicator of FIG. 6, illustrating the indicator in a third position.
Figure 7:
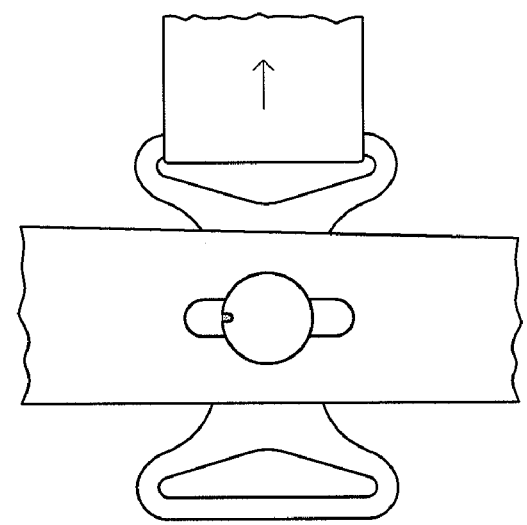
FIG. 7 is a right-side elevational view of the strap tension indicator of FIG. 6, illustrating the indicator in a second position.
Figure 6:
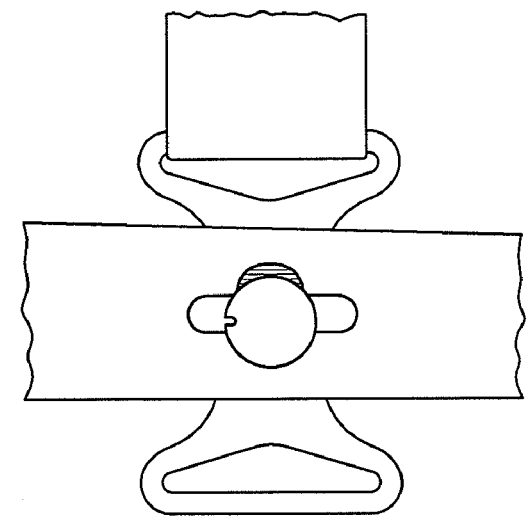
FIG. 6 is a right-side elevational view of another preferred embodiment of the present strap tension indicator, illustrating the indicator in a first position.

FIGS. 6-8 illustrate another preferred embodiment of the present strap tension indicator having three indicator positions. In this embodiment, the cap 84 includes a notch 92 that overlies a third lobe 94 of the marker label 76. The first and second lobes 80, 82 are both colored the same. For example, both the first and second lobes 80, 82 may be colored red. A central portion 96 (FIG. 7) of the third lobe 94 is colored a second color, such as green.

When the strap 33 is under minimal tension, as shown in FIG. 6, the red colored second lobe 82 is exposed, indicating that the strap tension is too low. As strap tension increases, the cap 84 slides across the marker label 76, covering the red colored second lobe 82. When the strap 33 reaches the optimal tension, as shown in FIG. 7, both the first and second red colored lobes 80, 82 are covered, and only the green colored central portion 96 of the third lobe 94 is visible through the notch 92 in the cap 84. If tension in the strap 33 increases beyond the optimal level, the cap 84 slides further across the marker label 76, covering the green colored central portion 96 of the third lobe 94 and uncovering the red colored first lobe 80, as shown in FIG. 8.

Those of skill in the art will appreciate that the present strap tension indicator may embody a variety of other configurations. For example, in the first embodiment described above, the green colored first lobe 80 may be eliminated and the red colored second lobe 82 retained. In this configuration, proper strap tension does not provide a colored visual indicator, while inadequate strap tension does. Vice versa, the green colored first lobe 80 may be retained and the red colored second lobe 82 eliminated. Similarly, the indicator may include multiple tension indication levels, such as a continuous tension scale. Further, any colors or symbols may be used to indicate inadequate tension, proper tension, and excessive tension. Rather than using colors to indicate tension, the indicator may use numbers, letters, or other symbolic indicator marks.

The compliance characteristics of the resilient member 54 are preferably selected so that proper strap tension moves the cap 84 into a position upon the marker label 76 such that the cap 84 exposes and/or covers various areas of the marker label 76 to indicate proper strap tension. Different straps in a given brace may have different optimal tensions. Thus, a given brace incorporating the present strap tension indicator may include a plurality of resilient members having different compliance characteristics. Similarly, for a given strap the optimal tension may change over a course of therapy.

Thus, it would be advantageous to be able to exchange one resilient member for another resilient member having different compliance characteristics, or to simply alter the compliance characteristics of a given resilient member. In certain embodiments of the present strap tension indicator, the components are readily disassembled so that the resilient member 54 may be modified or replaced. For example, if a bolt and nut are used to retain the various components of the strap tension indicator, the bolt and nut are easily unscrewed and reattached to one another.

Figure 9:
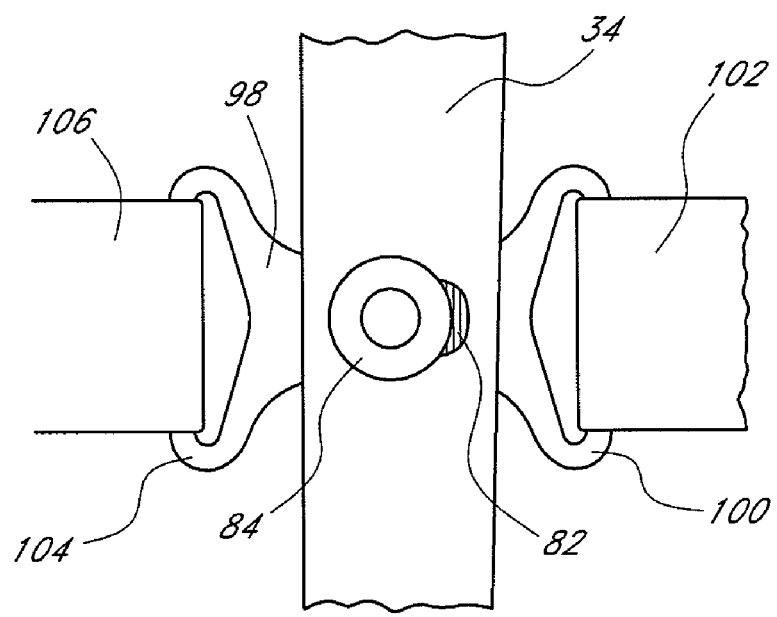
FIG. 9 is a right-side elevational view of another preferred embodiment of the present strap tension indicator, illustrating the indicator in a first position.
Figure 10:
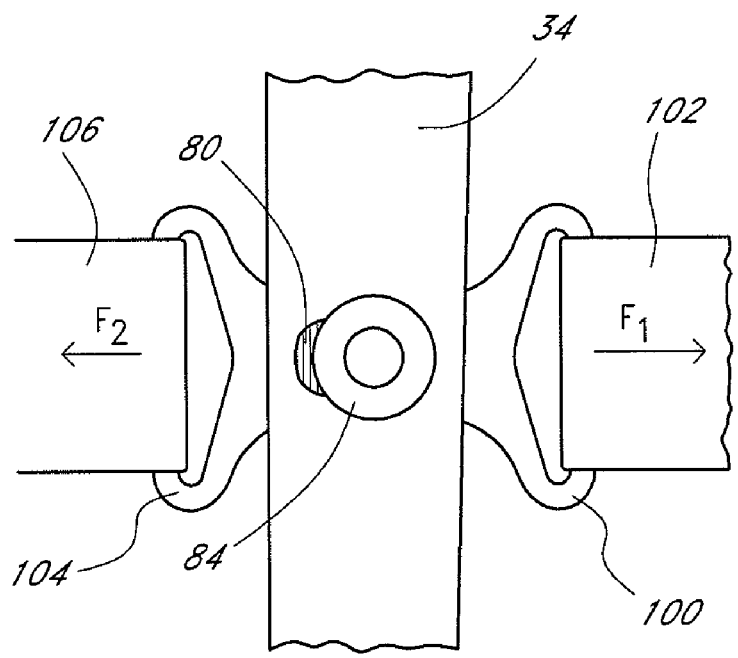
FIG. 10 is a right-side elevational view of the strap tension indicator of FIG. 9, illustrating the indicator in a second position.

In the embodiments of the present strap tension indicator illustrated above, the strap tab 66 includes only one loop portion 68 to which one strap 33 is attached. FIGS. 9 and 10 illustrate an alternative embodiment of the present strap tension indicator in which the strap tab 98 includes two oppositely extending loop portions. The first loop portion 100 includes an attached first strap 102, and the second loop portion 104 includes an attached second strap 106. The straps 102, 106 wrap in opposite directions around the wearer and exert forces on opposite sides of the wearer. As shown in FIG. 10, tension in the first strap 102 tends to pull the strap tab 98 in a first direction with a first force $F_1$. Tension in the second strap 106 tends to pull the strap tab 98 in a second direction, opposite the first direction, with a second force $F_2$. Thus, the tension indicator indicates the difference between the first force $F_1$ and the second force $F_2$.

In certain applications, the first force $F_1$ acting on the indicator of FIGS. 9 and 10 may be greater than the second force $F_2$ acting on the indicator. In certain other applications, the second force $F_2$ may be greater than the first force $F_1$. If the indicator comprises an aperture 36 and a resilient member 54 like those pictured in FIG. 4, then the greater of the first force $F_1$ and the second force $F_2$ preferably pulls the cap 84 toward the resilient member 54.

Figure 11:
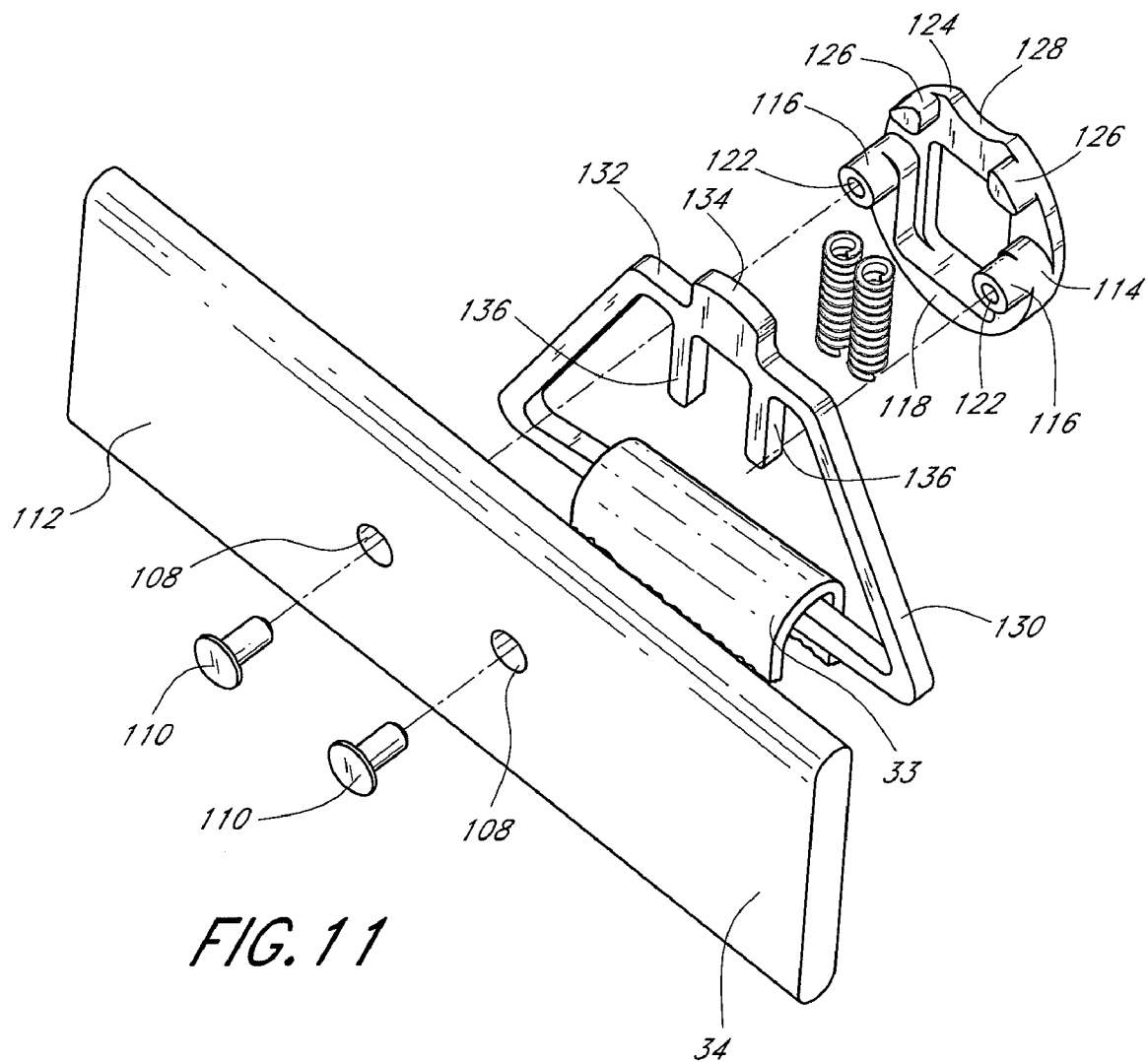
FIG. 11 is an exploded assembly view of another preferred embodiment of the present strap tension indicator, taken from a lower/front/left-side perspective.

FIGS. 11-16 illustrate another preferred embodiment of the present strap tension indicator. The indicator mounts a strap 33 to a rigid frame member 34 of a brace (not shown). With reference to FIG. 11, the frame member includes first and second spaced apertures 108. Fastening members 110 extend through the apertures 108 from a first side 112 (preferably facing toward the wearer) of the rigid frame member 34. The fastening members 110 may comprise, for example, rivets or bolts.

Figure 12:
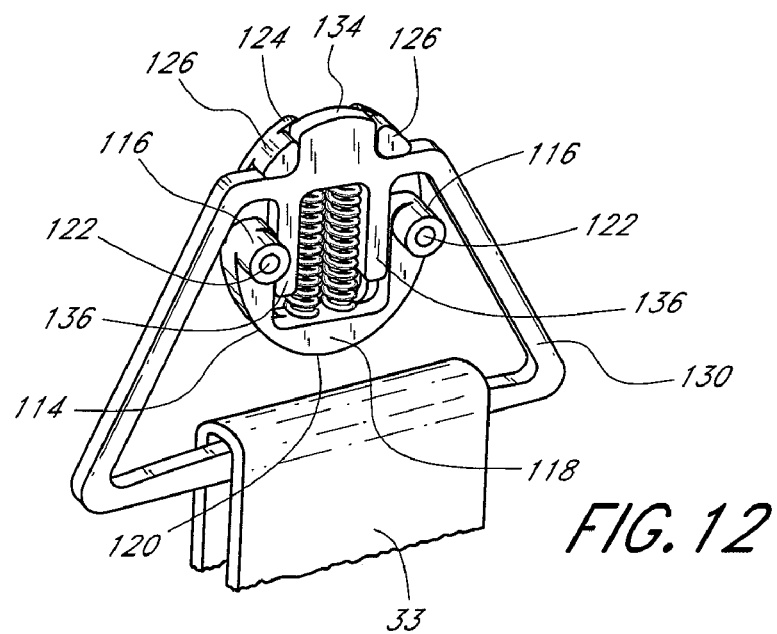
FIG. 12 is a perspective view of components of the strap tension indicator of FIG. 11, taken from a top/front/left-side perspective.
Figure 13:
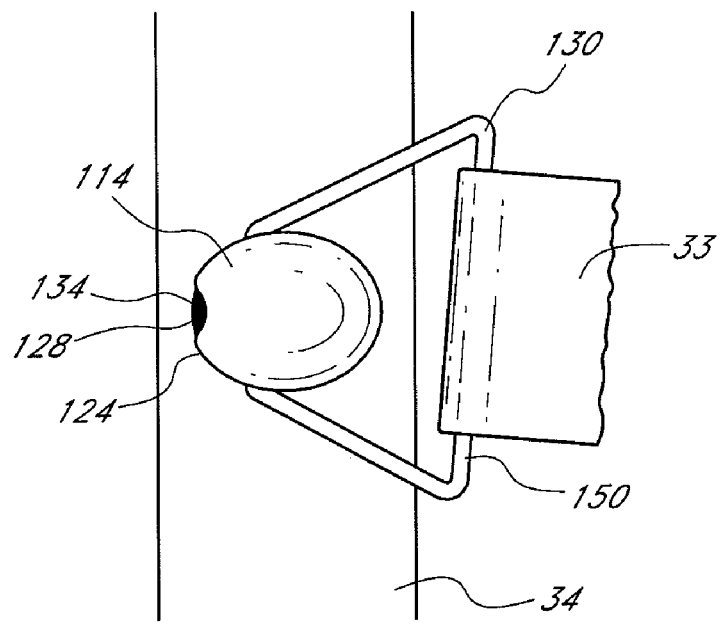
FIG. 13 is a right-side elevational view of the strap tension indicator of FIG. 11, illustrating the indicator in a first position.
Figure 14:
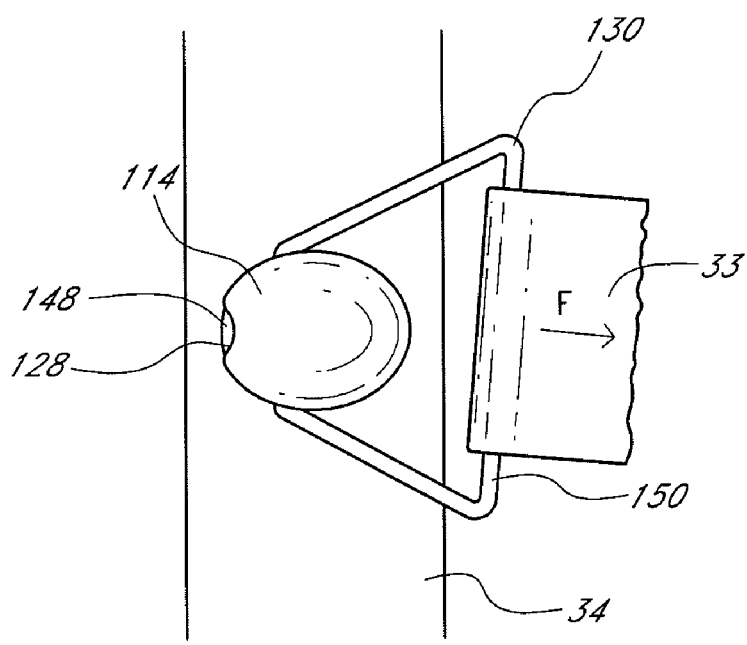
FIG. 14 is a right-side elevational view of the strap tension indicator of FIG. 11, illustrating the indicator in a second position.

The fastening members 110 engage a strap tab cap 114 that abuts a second side (preferably facing away from the wearer) of the rigid frame member 34. With reference to FIGS. 13 and 14, the strap tab cap 114 is substantially oval shaped in side elevational view. With reference to FIGS. 11 and 12, first and second posts 116 extend from a first surface 118 of the strap tab cap 114 that abuts the rigid frame member second surface. The first surface 118 is substantially U-shaped in side elevational view, such that the first surface 118 extends around a first end 120 (FIG. 12) of the oval-shaped strap tab cap 114 and along approximately half of each of the sides of the oval-shaped strap tab cap 114. Ends of the U-shaped first surface 118 terminate in the posts 116, such that the first and second posts 116 are located along edges of the strap tab cap 114 that are separated by a short axis of the oval. The first and second posts 116 are properly spaced to extend into the apertures 108 in the rigid frame member 34. The posts 116 include central countersunk holes 122 that receive the fastening members 110. The fastening members 110 secure the strap tab cap 114 to the rigid frame member 34. Those of skill in the art will appreciate that the strap tab cap 114 could be secured to the rigid frame member 34 using other methods, such as adhesives or welding. If such attachment methods are used, then the rigid frame member 34 need not necessarily include the apertures 108, and the strap tab cap 114 need not necessarily include the first and second posts 116.

With reference to FIGS. 11 and 12, a second end 124 of the oval-shaped strap tab cap 114, opposite the first end 120 and spaced from the posts 116, includes third and fourth posts 126. The third and fourth posts 126 extend from the strap tab cap 114 in the same direction as the first and second posts 116. The third and fourth posts 126 are spaced from one another along a line that is parallel to a line joining the first and second posts 116. A portion of the second end 124 of the oval-shaped strap tab cap 114, between the third and fourth posts 126, includes an indentation 128 (FIG. 11).

With reference to FIG. 11, the strap tab cap 114 secures a strap tab 130 to the rigid frame member 34. With reference to FIG. 12, the strap tab 130 is shaped substantially as a trapezoidal ring. The shorter parallel side 132 of the trapezoid includes a tab 134 that projects outwardly from the side 132 in substantially the same plane as the strap tab 130. The side 132 further includes a pair of spaced apart fingers 136 that project inwardly from the side 132 in substantially the same plane as the strap tab 130.

Figure 15:
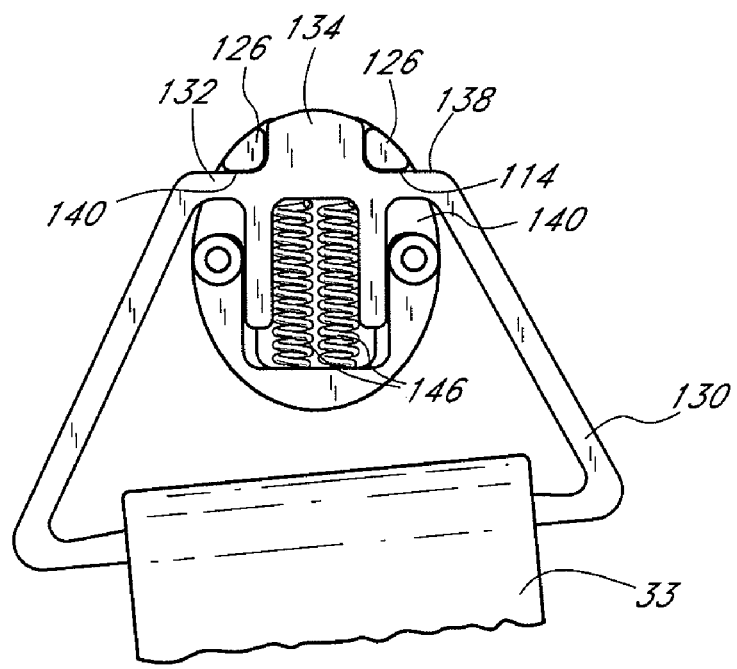
FIG. 15 is a left-side elevational view of components of the strap tension indicator of FIG. 11, illustrating the indicator in the first position.
Figure 16:
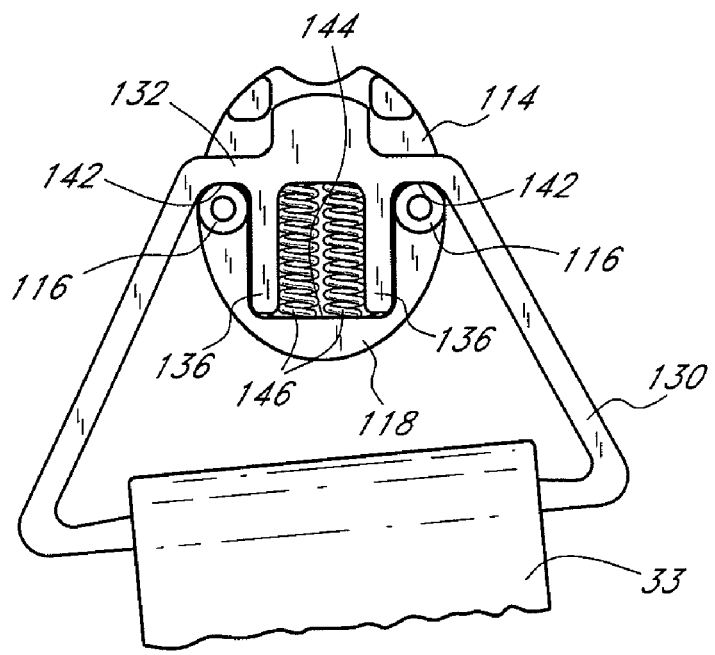
FIG. 16 is a left-side elevational view of the components of the strap tension indicator of FIG. 15, illustrating the indicator in the second position.

With continued reference to FIG. 12, the strap tab 130 is arranged relative to the strap tab cap 114 such that the shorter parallel side 132 extends across the strap tab cap 114 in a direction parallel to an imaginary line drawn between the first and second posts 116. Outer edges of the fingers 136 abut inner edges of the legs of the U-shaped first surface 118. With reference to FIGS. 15 and 16, the strap tab 130 is slidable with respect to the strap tab cap 114 between a first position (FIG. 15) and a second position (FIG. 16). In the first position, the outer edge 138 of the shorter parallel side 132 abuts inside surfaces 140 of each of the third and fourth posts 126, and the tab 134 resides between the third and fourth posts 126. In the second position, the inner edge 142 of the shorter parallel side 132 abuts the first and second posts 116 and ends of the fingers 136 preferably abut an inside surface 144 of the base portion of the U-shaped first surface 118.

A resilient member 146 biases the strap tab 130 toward the first position. In the illustrated embodiment, the resilient member 146 comprises a pair of coil springs. However, those of skill in the art will appreciate that the resilient member 146 could embody a variety of alternate constructions, such as a block of resilient material, such as polyurethane. A first end of each resilient member 146 abuts the inside surface 144 of the base portion of the U-shaped first surface 118. A second end of each resilient member 146 abuts the inside edge 142 of the shorter parallel side 132 of the strap tab 130.

With reference to FIGS. 13 and 14, when the strap tab 130 is in the first position (FIG. 13), the tab 134 extends beyond the concave edge of the indentation 128 in the second side 124 of the oval-shaped strap tab cap 114. When the strap tab 130 is in the second position (FIG. 14), no portion of the tab 134 extends beyond the edge of the indentation 128. A portion 148 of the rigid frame member 34 preferably bears a color that contrasts with the color of the tab 134.

The strap tab 130 and strap tab cap 114 together provide two indicator positions for indicating strap tension. In use, a strap 33 is secured to the longer parallel side 150 of the strap tab 130. Tension in the strap 33 pulls the strap tab 130 toward the second position with a force F, counteracting the force in the resilient member 146 that tends to push the strap tab 130 back toward the first position. By properly selecting a spring rate for the resilient member 146, the strap tab 130 moves to the second position only when the strap 33 is under the desired amount of tension. When the strap tab 130 moves to the second position, the displaced tab 134 exposes the colored portion 148 on the rigid frame member 34, thereby indicating that the strap is under the desired amount of tension.

SCOPE OF THE INVENTION

The above presents a description of the best mode contemplated for carrying out the present strap tension indicator for orthopedic brace, and of the manner and process of making and using it, in such full, clear, concise, and exact terms as to enable any person skilled in the art to which it pertains to make and use this strap tension indicator. This strap tension indicator is, however, susceptible to modifications and alternate constructions from that discussed above that are fully equivalent. Consequently, this strap tension indicator is not limited to the particular embodiments disclosed. On the contrary, this strap tension indicator covers all modifications and alternate constructions coming within the spirit and scope of the strap tension indicator as generally expressed by the following claims, which particularly point out and distinctly claim the subject matter of the strap tension indicator.

What is claimed is:

1. A strap tension indicator for an orthopedic brace, comprising:
    a rigid brace frame member including an aperture;
    a resilient member located within the aperture;
    a strap tab; and
    a fastening member partially within the aperture to secure the strap tab to the rigid brace member; wherein
    in a first position, the fastening member abuts the resilient member, and the strap tab and the fastening member are movable together toward a second position in which the resilient member tends to push the strap tab and the fastening member back toward the first position.

2. The strap tension indicator of claim 1, further comprising a strap, wherein the strap tab is connected to a first end of the strap.

3. The strap tension indicator of claim 2, wherein when the strap is under minimal tension, the fastening member occupies the first position, and as tension in the strap increases the strap tab and the fastening member move toward the second position.

4. The strap tension indicator of claim 1, wherein when the fastening member occupies the first position, the fastening member abuts a first side of the aperture.

5. The strap tension indicator of claim 4, wherein the aperture first side includes an indentation, and the fastening member seats within the indentation when the fastening member occupies the first position.

6. The strap tension indicator of claim 1, wherein the resilient member comprises a leaf spring.

7. The strap tension indicator of claim 6, wherein the leaf spring is V-shaped.

8. The strap tension indicator of claim 6, wherein the leaf spring includes multiple layers.

9. The strap tension indicator of claim 6, wherein the aperture is generally triangular.

10. The strap tension indicator of claim 9, wherein first and second end portions of the leaf spring abut peaks on second and third sides of the aperture.

11. The strap tension indicator of claim 10, wherein the second and third aperture sides between the peaks define a first boundary of a space, and the leaf spring defines a second boundary of the space, and when the fastening member moves toward the second position the area of the space decreases.

12. The strap tension indicator of claim 1, further comprising a strap tab cap, the fastening member passing through the cap to secure the cap to the rigid brace member.

13. The strap tension indicator of claim 12, wherein when the fastening member occupies the first position, the cap covers a first indicator portion on the rigid member.

14. The strap tension indicator of claim 13, wherein as the fastening member moves toward the second position, the cap exposes the first indicator portion.

15. The strap tension indicator of claim 12, wherein when the fastening member occupies the first position, the cap exposes a first indicator portion on the rigid member.

16. The strap tension indicator of claim 15, wherein as the fastening member moves toward the second position, the cap covers the first indicator portion.

17. The strap tension indicator of claim 12, wherein when the fastening member occupies the first position, the cap covers a first indicator portion on the rigid member and leaves a second indicator portion on the rigid member exposed.

18. The strap tension indicator of claim 17, wherein as the fastening member moves toward the second position, the cap exposes the first indicator portion and covers the second indicator portion.

19. The strap tension indicator of claim 12, wherein the indicator comprises a label marker secured to the rigid member.

20. The strap tension indicator of claim 12, wherein when the fastening member occupies the first position, the cap exposes a first portion of an indicator on the rigid member.

21. The strap tension indicator of claim 20, wherein when the fastening member occupies the second position, the cap exposes a second portion of the indicator.

22. The strap tension indicator of claim 1, further comprising a first indicator portion, a second indicator portion and a third indicator portion, wherein when the fastening member occupies the first position, the cap covers the first indicator portion and the third indicator portion, and leaves the second indicator portion exposed.

23. The strap tension indicator of claim 22, wherein as the fastening member moves toward the second position, the cap covers the second indicator portion, continues to cover the first indicator portion, and exposes the third indicator portion.

24. The strap tension indicator of claim 23, wherein as the fastening member moves past the second position, the cap covers the third indicator portion, continues to cover the second indicator portion, and exposes the first indicator portion.

25. A method of indicating the tension in a strap for an orthopedic brace, the method comprising the steps of:

providing an orthopedic brace having at least a first strap and a rigid brace member, the first strap including a strap tab that is secured to the rigid brace member and capable of moving with respect to the rigid brace member between a first position and a second position;

providing on the rigid brace member an indicator; and applying tension to the strap, which tension causes the strap tab to move from the first position towards the second position, thereby altering an appearance of the indicator.

26. The method of claim 25, wherein as the strap tab moves, a strap tab cap slides across the indicator, covering or exposing various portions of the indicator.

27. The method of claim 25, wherein the indicator includes at least a first portion providing a visual indication that tension in the strap is too low.

28. The method of claim 27, wherein the indicator includes at least a second portion providing a visual indication that tension in the strap is too high.

29. The method of claim 28, wherein the indicator includes at least a third portion providing a visual indication that tension in the strap is optimal.

30. A strap tension indicator for orthopedic brace, comprising:
a rigid brace frame member;
a strap tab slidably secured to the frame member, the strap tab being movable relative to the frame member between a first position and a second position; and
a resilient member; wherein
the resilient member biases the strap tab towards the first position.

31. The strap tension indicator of claim 30, further comprising a strap tab cap secured to the frame member.

32. The strap tension indicator of claim 31, wherein the strap tab and the strap tab cap cooperate to provide a first visual indication when the strap tab occupies the first position and to provide a second visual indication when the strap tab occupies the second position.

33. The strap tension indicator of claim 32, wherein the strap tab is slidable relative to the strap tab cap between the first position and the second position.

34. The strap tension indicator of claim 33, wherein the strap tab includes a tab that is visible when the strap tab occupies the first position, and that is hidden beneath the strap tab cap when the strap tab occupies the second position.

35. The strap tension indicator of claim 31, wherein the strap tab and the strap tab cap move together as the strap tab moves between the first position and the second position.

36. The strap tension indicator of claim 35, wherein when the strap tab occupies the first position the strap tab cap covers a first visual indicator and exposes a second visual indicator, and when the strap tab occupies the second position the strap tab cap covers the second visual indicator and exposes the first visual indicator.

37. The strap tension indicator of claim 31, wherein the strap tab may occupy a third position that is intermediate the first position and the second position.

38. The strap tension indicator of claim 37, wherein the strap tab and the strap tab cap cooperate to provide a first visual indication when the strap tab occupies the first position and to provide a second visual indication when the strap tab occupies the second position and to provide a third visual indication when the strap tab occupies the third position.

39. The strap tension indicator of claim 37, wherein the strap tab and the strap tab cap move together as the strap tab moves between the first position, the second position and the third position.

40. The strap tension indicator of claim 39, wherein when the strap tab occupies the first position the strap tab cap covers a first visual indicator, exposes a second visual indicator and covers a third visual indicator, and when the strap tab occupies the second position the strap tab cap exposes the first visual indicator, covers the second visual indicator and covers the third visual indicator, and when the strap tab occupies the third position the strap tab cap covers the first visual indicator, covers the second visual indicator and exposes the third visual indicator.

41. The strap tension indicator of claim 30, further comprising an orthopedic brace, wherein the strap tension indicator connects a strap of the brace to the rigid brace frame member.

42. The strap tension indicator of claim 41, wherein the brace is a knee brace.

43. A strap tension indicator for orthopedic brace, comprising:
a rigid brace frame member;
a strap tab slidably secured to the frame member, the strap tab being movable relative to the frame member between a first position and a second position;
means for indicating when the strap tab occupies the first position and when the strap tab occupies the second position; and
a resilient member; wherein
the resilient member biases the strap tab towards the first position.

44. The strap tension indicator of claim 43, wherein the means for indicating comprises a portion of the strap tab that cooperates with a strap tab cap, the strap tab cap alternately exposing and covering the portion of the strap tab as the strap tab moves between the first and second positions.

45. The strap tension indicator of claim 43, wherein the means for indicating comprises at least one portion on the rigid frame member that cooperates with a strap tab cap, the strap tab cap alternately exposing and covering the portion of the frame member as the strap tab moves between the first and second positions.

46. A strap tension indicator for orthopedic brace, comprising:
a rigid brace frame member including an aperture;
a resilient member located within the aperture;
a strap; and
a fastening member partially within the aperture to secure the strap to the rigid brace member; wherein
in a first position, the fastening member abuts the resilient member, and the strap and the fastening member are movable together toward a second position in which the resilient member tends to push the strap and the fastening member back toward the first position.

47. A strap tension indicator for orthopedic brace, comprising:
a rigid brace frame member;
a strap secured to the frame member, the strap being movable relative to the frame member between a first position and a second position; and
a resilient member; wherein the resilient member biases the strap towards the first position.

* * * * *